US010556052B2

(12) United States Patent
Turner (10) Patent No.: US 10,556,052 B2
(45) Date of Patent: Feb. 11, 2020

(54) CONTROL SYSTEM

(71) Applicant: Spectrum Medical Ltd., Gloucester (GB)

(72) Inventor: Stephen Turner, Gloucester (GB)

(73) Assignee: Spectrum Medical Ltd., Gloucester (GB)

(*) Notice: Subject to any disclaimer, the term of this patent is extended or adjusted under 35 U.S.C. 154(b) by 340 days.

(21) Appl. No.: 15/532,656

(22) PCT Filed: Dec. 3, 2015

(86) PCT No.: PCT/GB2015/053697
§ 371 (c)(1),
(2) Date: Jun. 2, 2017

(87) PCT Pub. No.: WO2016/087861
PCT Pub. Date: Jun. 9, 2016

(65) Prior Publication Data
US 2017/0361008 A1    Dec. 21, 2017

(30) Foreign Application Priority Data

Dec. 3, 2014  (GB) .................................. 1421498.5
Mar. 6, 2015  (GB) .................................. 1503805.2
Oct. 2, 2015  (GB) .................................. 1517433.7

(51) Int. Cl.
*A61M 1/16*    (2006.01)
*A61M 1/36*    (2006.01)

(52) U.S. Cl.
CPC ........ *A61M 1/1698* (2013.01); *A61M 1/3607* (2014.02); *A61M 1/3666* (2013.01);
(Continued)

(58) Field of Classification Search
CPC combination set(s) only.
See application file for complete search history.

(56) References Cited

U.S. PATENT DOCUMENTS 4,493,692 A    1/1985   Reed
5,810,759 A    9/1998   Merz
(Continued)

FOREIGN PATENT DOCUMENTS

EP    2 982 396    2/2016
GB    2485558      5/2012
(Continued)

OTHER PUBLICATIONS

Search Report under Section 17, Application No. GB1517433.7, dated Mar. 2, 2016, 1 page.
(Continued)

*Primary Examiner* — Leslie R Deak
(74) *Attorney, Agent, or Firm* — Sunstein Kann Murphy & Timbers LLP (57) ABSTRACT

A control system controlling blood gas values in blood processed by an oxygenator, wherein the oxygenator generates arterial blood by exposing venous blood to oxygen from an oxygenation gas supply, comprises a monitoring arrangement to determine a level of the blood gas values in the arterial blood and a controller that is responsive to the monitoring arrangement and configured to control parameters of the oxygenation gas supply to the oxygenator. This allows the blood gas values to be adjusted toward a predetermined level.

18 Claims, 5 Drawing Sheets

(52) U.S. Cl.
CPC ............... *A61M 2202/0208* (2013.01); *A61M 2205/3303* (2013.01); *A61M 2230/202* (2013.01); *A61M 2230/205* (2013.01)

(56) References Cited

U.S. PATENT DOCUMENTS

2009/0182258 A1  7/2009  Sanches et al.
2011/0129389 A1  6/2011  Brady et al.

FOREIGN PATENT DOCUMENTS

WO  WO 2011/021978  2/2011
WO  WO 2011/066481  6/2011

OTHER PUBLICATIONS

Martin J. Amezaga, Authorized officer European Patent Office International Search Report—Application No. PCT/GB2015/053697, dated Feb. 17, 2016, 12 pages, together with the Written Opinion of the International Searching Authority.

Fig. 7

CONTROL SYSTEM

FIELD OF THE INVENTION

The present invention relates to a control system for controlling parameters of a perfusion system. More specifically, the present invention relates to apparatus and methods comprising a closed loop control to maintain blood gas parameters during extracorporeal blood oxygenation.

BACKGROUND

Certain medical procedures require the heart or lung of a patient to be kept still. This may be necessary in order for a surgeon to perform surgical procedures, such as cardiac surgery. While the heart is unable to circulate blood or the lung is unable to re-oxygenate blood or to remove carbon dioxide, heart-lung machines are used for life support, providing extracorporeal oxygenation to maintain a supply of oxygen to a patient.

More recently, extracorporeal oxygenation has been explored for the management of viral infections (such as H1N1) that affect lung function by causing pulmonary embolisms. Patients suffering from such infections may require long-term ventilation, in the region of several weeks (typically 20 days, but in severe cases ventilation may be required for several months, e.g. for up to 180 days), in order to facilitate treatment and drainage of the lung, and in order to permit the lung to rest and heal while the patient's immune system is given an opportunity to defeat the viral infection.

The partial pressures of oxygen and carbon dioxide, pO2 and pCO2, are indicative of physiological activity and, thus, of interest for extracorporeal oxygenation management. PCT-published application WO2012066280 by the present applicant discloses a method and apparatus for determining pO2 and/or pCO2 as a function of, inter alia, the amount of carbon dioxide CO2 entering and exiting a ventilation machine. United Kingdom patent application number GB1503805.2 by the present applicant describes methods and apparatus for determining the partial pressure of oxygen pO2 as a function of, inter alia, the oxygen uptake in an oxygenator.

The present invention seeks to provide improved options for ventilation management.

SUMMARY OF THE INVENTION

In accordance with a first aspect of the invention, there is disclosed a control system controlling one or more blood gas values in blood processed by an oxygenator, as defined by claim 1.

The control system is suitable for an oxygenator of an extracorporeal perfusion system, i.e., for an oxygenator of the type configured to generate arterial blood by exposing venous blood to oxygen from an oxygenation gas supply.

The control system comprises a monitoring arrangement to determine a level of the one or more blood gas values in the arterial blood, and a controller responsive to the monitoring arrangement, wherein the controller is configured to control parameters of the oxygenation gas supply to the oxygenator, to adjust one or more of the blood gas values toward a pre-determined level.

It will be appreciated that the oxygenator receives an oxygenation gas supply via an external supply system. The oxygenation gas comprises oxygen; it may also consist of pure oxygen. The oxygen transfer in the oxygenator from the oxygenation gas to venous blood depends on factors such as the flow rate of the oxygenation gas supply and the fraction of oxygen in the oxygenation gas supply.

Unused gas of the gas supply and excess gases leave the oxygenator as exhaust gas. Properties of the exhaust gas may be indicative of the oxygenation performance (e.g., how much oxygen was taken up by the blood in the oxygenator). However, deriving information on the oxygenation performance based on exhaust gas properties is not trivial, because oxygenators are not air-tight. It cannot necessarily be assumed that gas leaving an oxygenator port is constituted only of unused oxygenation supply gas.

A controller responsive to the monitoring arrangement can be regarded as a closed loop control. This provides a more responsive mechanism for maintaining blood gas values at a pre-determined level.

Blood gas values of a patient may change even though perfusion parameters remain constant. For instance, the body temperature or metabolic activity of a patient may change. This will affect the oxygen consumption. Thus, the venous blood entering the perfusion system may have different blood gas properties. By modulating perfusion parameters to adjust the blood gas values of the arterial blood before this is provided to a patient, a mechanism is provided that allows oxygenated blood to be provided with blood gas values at a steady, pre-determined level, or within pre-determined boundaries.

This improves reaction times. This reduces fluctuations of supply conditions of arterial blood that is prepared for subsequent administration to a patient.

In embodiments, the blood gas values comprise the partial pressure of oxygen in the arterial blood and/or the partial pressure of carbon dioxide in the arterial blood.

In embodiments, the controller comprises a configuration permitting it to alter the composition of the oxygenation gas supplied to the oxygenator.

The partial pressure of oxygen in the arterial blood can be influenced by the composition of the oxygenation gas, because the partial pressure of oxygen depends on the fraction fiO2 of oxygen in the oxygenation gas (and also on the flow rate of the oxygenation gas) supplied into the oxygenator.

In embodiments, the controller comprises a configuration permitting it to alter the flow rate of the oxygenation gas supplied to the oxygenator.

The partial pressure of carbon dioxide in the arterial blood can be influenced by the flow rate of the oxygenation gas, because the partial pressure of carbon dioxide depends on the flow rate of the oxygenation gas supplied into the oxygenator.

In embodiments, the controller is configured to adjust the partial pressure of carbon dioxide in the arterial blood by altering the flow rate of the oxygenation gas supply.

In embodiments, the controller is configured to adjust the partial pressure of oxygen in the arterial blood by altering the fraction of oxygen in the oxygenation gas supply.

Adjusting the partial pressure of oxygen by altering the oxygen fraction in the oxygenation gas provides some independence in controlling other parameters. E.g. the flow rate may be changed to adjust the partial pressure of carbon dioxide in the oxygenation gas supply.

In embodiments, the controller comprises decision logic to determine a difference between the level of the blood gas value and the pre-determined level, and to determine oxygenation gas supply parameters suitable for reducing the difference.

This allows the feedback loop to respond in proportion to the difference. This provides a more responsive feedback mechanism.

In embodiments, the decision logic is configured to reduce the difference by calculating an offset value representing a change in oxygenation gas supply parameters suitable for reducing the difference.

This further improves the responsiveness of the feedback loop.

In embodiments, the pre-determined level is a pre-determined partial pressure of carbon dioxide in the arterial blood, and the oxygenation gas supply parameters comprise a flow rate suitable for reducing the difference.

In embodiments, the pre-determined level is a pre-determined partial pressure of oxygen in the arterial blood, and the oxygenation gas supply parameters comprise a fraction of oxygen suitable for reducing the difference.

In embodiments, the monitoring arrangement comprises a configuration permitting it to simultaneously determine levels of a plurality of blood gas values.

For instance, the monitoring arrangement may comprise a configuration permitting it to simultaneously determine both the partial pressure of oxygen in the arterial blood and the partial pressure of carbon dioxide in the arterial blood.

The relationship between the oxygenation gas supply condition and the blood gas parameters in the arterial blood may be complex. For instance, a change in the flow rate of oxygenation gas affects the partial pressures of both carbon dioxide and oxygen. This has to be taken into account, e.g., if the partial pressure of carbon dioxide is to be adjusted by a different amount than the partial pressure of oxygen. Measuring a plurality of blood gas values simultaneously provides a basis for determining adjustment parameters to be calculated for each blood gas value while taking into account potential effects on other blood gas values.

In embodiments, the controller is configured to simultaneously control a plurality of parameters of the oxygenation gas supply to the oxygenator, to simultaneously adjust levels of a plurality of blood gas values.

For instance, the controller may be configured in this manner to simultaneously adjust the partial pressure of oxygen in the arterial blood and the partial pressure of carbon dioxide in the arterial blood.

The partial pressure of oxygen in the arterial blood can be influenced by the flow rate of the oxygenation gas and by the fraction of oxygen in the oxygenation gas. The partial pressure of carbon dioxide in the arterial blood can be influenced by the flow rate of the oxygenation gas. The partial pressures of oxygen and of carbon dioxide may be influenced simultaneously by setting the flow rate of the oxygenation gas to a level suitable for adjusting the partial pressure of carbon dioxide, and at the flow rate, setting the fraction of oxygen in the oxygenation gas to a level suitable for adjusting the partial pressure of oxygen.

In embodiments, the monitoring arrangement is configured to determine the one or more blood gas values without contacting blood.

Using blood gas analysis algorithms and flow control systems described herein, the blood gas values (partial pressures of oxygen and/or carbon dioxide in the arterial blood) may be determined without contacting blood.

The determination of the blood gas values may be on the basis of estimates corrected by a calibration step, as set out below.

In embodiments, the monitoring arrangement is configured to determine the one or more blood gas values continuously.

This improves the responsiveness of the closed loop control.

In accordance with a second aspect of the invention, there is disclosed a method of controlling one or more blood gas values in blood processed by an oxygenator, as defined by claim 15.

The method is suitable for an oxygenator of an extracorporeal perfusion system, i.e., for an oxygenator of the type configured to generate arterial blood by exposing venous blood to oxygen from an oxygenation gas supply.

The method comprises the steps of determining a level of each of the one or more blood gas values in the arterial blood, and controlling, in response to the level, parameters of the oxygenation gas supply to the oxygenator, to adjust one or more of the blood gas values toward a pre-determined level.

In embodiments, determining a level of one or more blood gas values comprises monitoring the partial pressure of oxygen in the arterial blood and/or the partial pressure of carbon dioxide in the arterial blood.

In embodiments, the method further comprises altering the composition of the oxygenation gas supplied to the oxygenator.

In embodiments, the method further comprises altering the flow rate of the oxygenation gas supplied to the oxygenator.

In embodiments, the method further comprises adjusting the partial pressure of carbon dioxide in the arterial blood by altering the flow rate of the oxygenation gas supply.

In embodiments, the method further comprises adjusting the partial pressure of oxygen in the arterial blood by altering the fraction of oxygen in the oxygenation gas supply.

In embodiments, the method further comprises determining a difference between the level of the blood gas value and the pre-determined level, and determining oxygenation gas supply parameters suitable for reducing the difference.

In embodiments, the method further comprises calculating an offset value representing a change in oxygenation gas supply parameters suitable for reducing the difference, and determining the oxygenation gas supply parameters on the basis of the offset value.

In embodiments, the method further comprises determining the difference between the level of the partial pressure of carbon dioxide in the arterial blood and the pre-determined level of the partial pressure of carbon dioxide in the arterial blood, and determining an oxygenation gas flow rate suitable for reducing the difference.

In embodiments, the method further comprises determining the difference between the level of the partial pressure of oxygen in the arterial blood and the pre-determined level of the partial pressure of oxygen in the arterial blood, and determining an oxygenation gas oxygen fraction suitable for reducing the difference.

In embodiments, the method further comprises simultaneously determining levels of a plurality of blood gas values.

In embodiments, the method further comprises simultaneously controlling a plurality of parameters of the oxygenation gas supply to the oxygenator, to simultaneously effect an adjustment of levels of a plurality of blood gas values.

In embodiments, the method further comprises determining the one or more blood gas values without contacting blood.

In embodiments, the method further comprises determining the one or more blood gas values continuously.

DESCRIPTION OF THE FIGURES

Exemplary embodiments of the invention will now be described with reference to the Figures, in which.

DESCRIPTION

By way of background, an oxygenator is a device configured to receive oxygenation gas and venous blood, to re-oxygenate the blood by exposure to the oxygenation gas, and to provide oxygenated blood as arterial blood. Unused oxygenation gas is vented as exhaust gas which will also carry any gas given away by the blood.

Herein, the oxygenation gas is referred to as "inlet gas" with reference to the oxygenator. Note that in some literature the same oxygenation gas may be referred to differently (e.g. as "exit gas" with reference to a gas source). Herein, exit gas or exhaust gas denotes gas leaving the oxygenator. An oxygenator setup will be described in more detail with reference to FIGS. 2 to 4 below.

Theory and Principle of the Determination of the Partial Pressure of Oxygen

For the understanding of some embodiments, described herein are several unconventional variants of methods of analysing blood gas parameters to better determine the partial pressure of oxygen of arterial blood leaving an oxygenator.

Herein, such unconventional methods may be referred to as a "blood analysis methods". The blood analysis methods disclosed herein are described in the applicant's co-pending United Kingdom patent application number GB1503805.2.

The present applicant has appreciated that a good estimate of the partial pressure of oxygen in arterial blood can be obtained by first determining an initial estimate of the partial pressure of oxygen in the exhaust gas, and by adjusting the initial estimate based on the oxygen uptake by the blood passing the oxygenator. The blood oxygen uptake can be determined with optical sensors. Herein, optical sensors are regarded as non-contact sensors because the optical radiation does not require physical contact with blood.

This allows the partial pressure of oxygen in blood to be determined without requiring a sensor coming into contact (such as the Clark electrode) and without an external contrast agent to be injected into the blood.

Determining pO2 Via Blood Oxygen Take-Up

Oxygenation gas (a mixture of gas components including oxygen) is supplied to an oxygenator at an inlet gas flow rate GI with an oxygen fraction fiO2 and a carbon dioxide fraction fiCO2.

In the oxygenator, oxygen O2 from the inlet gas is taken up by blood. The remaining gas leaves the oxygenator as exhaust gas through an exhaust port (an exhaust port in principle, as there are also ventilation ports, as explained below) at an exhaust gas flow rate GE. Knowledge of the fraction feO2 of oxygen GEO2 in the exhaust gas GE would be desirable because this is directly related to the partial pressure $pO2_{GE}$ of oxygen O2 in the exhaust gas and the atmospheric (ambient) pressure Patm.

$$pO2_{GE} = feO2 \times Patm \quad (1)$$

$$feO2 = GEO2/GE \quad (2)$$

Equivalent considerations apply to the partial pressure $pCO2_{GE}$ of carbon dioxide CO2 in the exhaust gas GE.

$$pCO2_{GE} = feCO2 \times Patm \quad (3)$$

$$feCO2 = GECO2/GE \quad (4)$$

Flow rates GE, GEO2 and GECO2 may be referred to as "amounts" in day-to-day language, but are conventionally measured in L/min. The fractions feO2 and feCO2 are given as a percentage.

It follows that the partial pressure $pO2_{GE}$ may be calculated by determining the proportion of the amount GEO2 (of oxygen O2 in the exhaust gas GE) relative to relation to the exhaust gas GE.

However, the exhaust gas flow rate GE measured at the exhaust port of an oxygenator housing is not directly related to the total gas exiting the gas-blood interface (the gas-blood interface typically being provided in the form of hollow fibres) inside the oxygenator, because oxygenators are not air-tight. For safety reasons, an oxygenator housing comprises ventilation ports that prevent a pressure increase in the event of a blockage of the exhaust port. Such a pressure increase could lead, for example, to life-threatening gaseous blood emboli. Thus, the exhaust gas flow rate GE, if measured at the oxygenator exhaust port, may be affected by gas flow through ventilation ports and will not necessarily provide an accurate indication of the total exhaust gas given away from the gas-blood interface inside the oxygenator.

The present applicant has appreciated that it is possible to determine the fraction feO2 of oxygen O2 in the exhaust gas GE as the difference between (a) the oxygen supplied to the oxygenator as inlet gas oxygen GIO2 and (b) the oxygen taken up by the blood in the oxygenator. The oxygen take-up in the oxygenator can be described as the difference between the amount of oxygen in the arterial blood BEO2 (exiting the oxygenator in an oxygen-enriched state) and the venous blood BIO2 (entering into the oxygenator in an oxygen-decreased state).

Thus, the amount GEO2 of oxygen O2 in the exhaust gas GE is described by the difference between the amount of oxygen GIO2 supplied to the oxygenator and the amount of oxygen taken up by the blood (BEO2−BIO2).

$$GEO2 = GIO2 - (BEO2 - BIO2) \quad (5)$$

The values GIO2 and (BEO2−BIO2) are now considered in turn.

Oxygen Supply GIO2

The inlet gas flow rate GIO2 of oxygen O2 and the inlet gas flow rate GICO2 of carbon dioxide CO2 are a fraction fiO2 or fiCO2, respectively, of the total inlet gas flow rate GI. The fraction fiO2 of oxygen and the fraction fiCO2 of carbon dioxide relative to the atmospheric pressure determine the partial pressure of oxygen or carbon dioxide, $pO2_{GI}$ and $pCO2_{GI}$, respectively.

$$GIO2 = GI \times fiO2 \quad (6)$$

$$fiO2 = pO2_{GI}/Patm \quad (7)$$

$$GICO2 = GI \times fiCO2 \quad (8)$$

$$fiCO2 = pCO2_{GI}/Patm \quad (9)$$

The factors at the right-hand side of equations 6 to 9 may be measured as follows:

GI may be measured by a pressure drop technique (the higher the flow, the higher the pressure drop). To provide an illustrative example, the inlet gas flow rate may be measured using a mass flow meter or any other suitable method, e.g., a Venturi tube or an orifice plate. The units of the flow rate are usually L/min (1 min=60 seconds), but it is understood that other units may be used.

The partial pressure $pCO2_{GI}$ of carbon dioxide in the inlet gas may be measured with an optical (non-contact) sensor that provides an output indicative of the partial pressure $pCO2_{GI}$ of carbon dioxide CO2 in the inlet gas. fiCO2 is calculated according to equation 9. fiCO2 is dimensionless and typically given as a percentage.

The partial pressure pO2, of oxygen in the inlet gas may be measured with a galvanic cell type oxygen sensor. A galvanic cell type oxygen sensor produces a voltage which is proportional to the partial pressure of oxygen in the inlet gas, and so is proportional to both the oxygen concentration and the gas pressure. The oxygen sensor may be calibrated with calibration gases having a known O2 fraction. For instance, readings may be obtained for two calibration gases, each having an externally verified oxygen content. A first calibration gas may have an oxygen fraction of 21% (v/v, in air). A second calibration gas may have 100% oxygen (i.e., for practical purposes, pure oxygen). The oxygen sensor may take a first O2 sensor reading of the first calibration gas. The oxygen sensor may take a second O2 sensor reading of the second calibration gas. The ambient gas pressure Patm may also be measured so that it may be taken into account when calibrating the sensor. In operation, the sensor reading is thus relatable to values of known oxygen content values, and also the ambient gas pressure can be taken into account. fiO2 is a percentage value.

Patm may be obtained, for instance, via a direct measurement from an integrated sensor, and/or provided as an input parameter. For instance, Patm may be measured at the inlet or at the outlet of an oxygenator. A typical Patm value is in the region of 1013 mbar (1 atm).

The sensors for measuring the total inlet gas flow GI, the inlet gas oxygen fraction fiO2, and the inlet gas carbon dioxide fraction fiCO2 may be provided in a sensor unit. The sensors may be integrated into a single sensor unit. Conveniently, the sensor unit may be installed at the oxygenation gas inlet into the oxygenator. Exemplary measurement systems that are suitable for this purpose include the Spectrum System M™ range of diagnostic monitors available from Spectrum Medical Ltd, of Gloucester, GL2 9QL, England (the applicant of the present specification). The sensor unit may also comprise a sensor for measuring atmospheric pressure Patm.

Blood Oxygen Uptake (BEO2−BIO2)

In conditions where the supply GIO2 of oxygen into the oxygenator is relatively low, e.g. due to a low fiO2 fraction and/or a low inlet gas flow rate GI (known as "sweep"), the use of oxygen by a patient may be large enough to significantly lower the oxygen content of the gas. Therefore, in order to ensure that the algorithm for estimating GEO2 is applicable to a wide range of clinical scenarios, including scenarios with low oxygen supply, a more accurate estimate can be obtained by taking into consideration the oxygen consumption by the patient, by way of the term BEO2−BIO2.

In the oxygenator, the exchange of oxygen O2 between the oxygenation gas and the blood depends on the partial oxygen pressures pO2, namely the partial oxygen pressure in the oxygenation gas, and the partial pressure $pO2_{BLOOD}$ in the blood: a higher gas partial oxygen pressure causes more oxygen to dissolve in blood and increases the blood partial oxygen pressure. In the absence of other influences the partial pressures will over time reach equilibrium. A notable property of blood is that oxygen will be bound by haemoglobin. The relationship between haemoglobin-bound oxygen and the blood partial oxygen pressure is complex, and the oxygen-binding properties of haemoglobin are dependent on various factors, such as temperature, pressure, blood pH, etc., which are omitted in this explanation for simplicity. As a simplification, it can be assumed that, once bound to haemoglobin, an oxygen molecule no longer contributes directly to the blood partial oxygen pressure. Thus, the total amount of oxygen in blood includes oxygen dissolved in blood plasma, which determines the blood partial oxygen pressure $pO2_{BLOOD}$, and oxygen bound to haemoglobin, which does not contribute to $pO2_{BLOOD}$. Haemoglobin binds oxygen highly effectively and at physiological haemoglobin concentrations the amount of haemoglobin-bound oxygen exceeds the plasma-dissolved oxygen significantly.

For the determination of arterial blood BEO2 and venous blood BIO2 it can be assumed that the oxygen taken away from the inlet gas by dissolving directly in the blood plasma is negligible compared to that bound to haemoglobin. The present applicant has appreciated that, as a simplification, it can be assumed that oxygen in the inlet gas decreases only by binding to haemoglobin. Likewise, it can be assumed that an increase in haemoglobin-bound blood oxygen inside the oxygenator corresponds to the consumption of inlet gas oxygen.

The amount of oxygen bound to haemoglobin in a given volume of blood depends on the number of oxygen binding sites and, thus, the number of haemoglobin molecules per volume of blood and the level of oxygen saturation of the oxygen binding sites. Thus, the amount BIO2 of oxygen O2 in the venous blood BI and the amount BEO2 of oxygen O2 in the arterial blood BE can be expressed as:

$$BIO2 = Hb \times 0.1551 \times Q \times 4 \times SvO2/100 \quad (10)$$

$$BEO2 = Hb \times 0.1551 \times Q \times 4 \times SaO2/100 \quad (11)$$

The values of the blood flow Q, the arterial oxygen saturation SaO2, the venous oxygen saturation SvO2, and the haemoglobin concentration Hb, can be obtained by non-contact measurement (examples described below). Conventionally, BIO2, BEO2, and Q are provided in L/min (1 min=60 seconds), Hb in g/dl (1 dl=0.1 L), and SaO2 and SvO2 percent. As an aside, one mol of haemoglobin weighs 64,458 g. It follows that 1 g of haemoglobin comprises 0.01551 mol, and a factor of 0.1551 allows g/dl to be converted to mmol/L. In equations 10 and 11, the factor 4 accounts for the number of oxygen molecules that can bind to each molecule of haemoglobin.

Blood flow Q may be measured by any suitable means, e.g., a Doppler flow meter or by determining the positive displacement of a peristaltic roller pump. The unit of the flow rate Q is usually L/min.

Oxygen saturation SO2 (both arterial oxygen saturation SaO2 and venous oxygen saturation SvO2) and haemoglobin Hb may be measured by a non-contact optical measurement method locatable at a suitable position of the oxygenator. Exemplary optical measurements use LEDs and multiple-wavelength light sensors to determine blood absorption characteristics (the redness of blood changes depending on the haemoglobin oxygenation state). The unit of saturation is dimensionless and typically given percent. The haemoglobin concentration is conventionally provided in g/dl.

An exemplary measurement system that is capable of measuring the flow rate Q, haemoglobin concentration Hb, and both the arterial and venous oxygen saturation is the Spectrum System M™ range of diagnostic monitors available from Spectrum Medical Ltd, of Gloucester, GL2 9QL, England (the applicant of the present specification).

It is possible to determine BIO2 and BEO2 without contacting the blood via equations 10 and 11 when non-contact sensors are used to measure Q, Hb, SaO2 and SvO2. This is an advantage over using a contact electrode such as a Clark-type electrode. Even if, e.g., a conventional Clark-type electrode were to be used as a reference sensor for calibration prior to use, this avoids having to bring a blood sensor in direct blood contact during continual measurements of the quantities Q, Hb, SaO2 and SvO2. Of course, equations 10 and 11 are not limited to non-contact sensors; any suitable sensor may be used to measure these quantities.

It can further be assumed that during a relevant time scale the amount of haemoglobin in the venous blood (entering the oxygenator) and in the arterial blood (leaving the oxygenator) remains steady, as does the blood flow rate Q. Therefore, the blood oxygen uptake (BEO2−BIO2) can be described by equation 12:

$$(BEO2-BIO2)=Hb\times 0.1551\times Q\times 4\times (SaO2-SvO2)/100 \quad (12)$$

This allows the values BEO2 and BIO2 to be determined using a sensor for the blood flow Q and/or or the haemoglobin concentration Hb at a single location. For the avoidance of doubt, two sensors are used for the oxygen saturation measurements, one for arterial oxygen saturation SaO2 and one for venous oxygen saturation SvO2.

Relating the Amount GEO2 of Oxygen in the Exhaust Gas to the Fraction feO2

Via equation 5, the amount GEO2 of oxygen O2 in the exhaust gas GE can be determined without an exhaust gas sensor. Knowledge of the exhaust gas flow GE is then required to solve equations 2 and 4.

Direct Determination of Exhaust Gas Flow GE

Later in the present specification a description will follow of a non-conventional perfusion system design that allows the flow rate GE out of a main exhaust port of the oxygenator to be controlled. This provides a route to determining GE from the control parameters.

Indirect Determination of Exhaust Gas Flow GE

However, with conventional oxygenators it is not possible to control the exhaust gas flow rate. As described above, because oxygenators are not closed systems, the exhaust gas flow GE measured at a conventional oxygenator exhaust port does not provide an accurate indication of the amount of exhaust gas exiting the gas-blood interface inside the oxygenator. An alternative to directly determining the exhaust flow rate GE is presented in the following passages of the present description.

The exhaust gas GE transported away from the oxygenator is assumed to consist of O2, CO2, and N2. Any amount of water H2O is assumed to be negligible. Likewise, any amount of substantially insoluble gases, such as noble gases and common fluorinated anaesthetic agents, is assumed to be either negligible or as included with the nitrogen term N2 for the purposes of pO2 prediction.

$$GE=GEO2+GECO2+GEN2 \quad (13)$$

GEO2 is determined via equation 5.

GECO2: According to equation 4, the amount GECO2 of carbon dioxide in the exhaust gas depends on the fraction feCO2 of carbon dioxide and the amount of exhaust gas GE. However, as will be shown in equations 17 to 19 below, a direct measurement of the fraction feCO2 of the carbon dioxide CO2 in the total exhaust gas flow GE will suffice for the purpose of determining an estimate of GE. The feCO2 sensor may be a stand-alone sensor at the exhaust port of the oxygenator.

GEN2: It is assumed that the amount of N2, and of any inert or largely insoluble gas, remains constant during oxygenation, i.e., that N2 is neither taken up nor given away by the blood.

$$GEN2=GIN2 \quad (14)$$

For a determination of GIN2, it is assumed that the gas mixture GI consists only of O2, CO2, and N2, whereas the amount of water H2O and the amount of noble gases can be regarded as negligible and/or as included with the GIN2 term.

$$GI=GIO2+GICO2+GIN2 \quad (15)$$

By substituting right-hand terms of equation 15 with equations 6 and 8, the flow rate GIN2 of nitrogen N2 can be expressed as:

$$GIN2=GI\times [1-(fiO2+fiCO2)] \quad (16)$$

The right-hand terms of equation 16, GI, fiO2, and fiCO2, can be measured by sensors at the oxygenator inlet as described above, avoiding a need for a separate measurement of the amount GIN2 of nitrogen N2 in the inlet gas GI or of the amount GEN2 in the outlet gas GE.

Thus, a sufficiently representative estimate of the outlet gas flow GE can be determined by substituting right-hand terms of equation 13 using equation 5 (for GEO2), equation 4 (for GECO2), and equations 14 and 16 (for GEN2).

$$GE=GEO2+GIN2+(feCO2\times GE) \quad (17)$$

$$\text{Thus, } GE-(feCO2\times GE)=(GEO2+GIN2) \quad (18)$$

$$\text{Thus, } GE=(GEO2+GIN2)/(1-feCO2) \quad (19)$$

The fraction feCO2 of carbon dioxide in the exhaust gas can be assumed to be accurately determined by a direct sensor measurement from the main oxygenator exhaust port.

Having determined an estimate of GE via equation 19, the partial pressure $pO2_{GE}$ of oxygen in the exhaust gas can be obtained via equations 1 and 2.

Further Increasing the Accuracy of pO2GE

By way of background, the inlet flow rates in L/min can be converted into mmol/min by assuming ideal gas conditions and that, therefore, 1 mol of gas occupies 22.41 L at standard temperature and pressure (STAP). The system may be configured to adjust for measured gas pressure. In practice, sufficient accuracy can be achieved by assuming that the ambient air has a temperature of 20° C. Alternatively, the ambient temperature may be measured by a sensor, allowing the temperature to be considered when converting L/min to mmol/min.

Blood temperature affects the partial pressure $pO2_{BLOOD}$ of blood oxygen. It was found by the applicant that it is possible to account for temperature effects by applying a linear offset, temperature term $\text{offset}_{TEMP}$, that correlates with blood temperature $T_{BLOOD}$ $$\text{offset}_{TEMP}=2\times(37-T_{BLOOD}) \quad (20)$$

The blood temperature $T_{BLOOD}$ is the temperature of the blood entering or exiting the oxygenator in celsius. The blood temperature may be measured by any suitable thermometer. The thermometer may be located at a suitable location.

When calculating the oxygen uptake BEO2-BIO2 in the afore-described manner, simplifying assumptions are made about the oxygenator efficiency. The simplifying assumptions ignore that oxygen saturation is influenced by factors including the exchange area available for oxygenation, the blood flow rate (the slower the flow rate, the more time to approach equilibrium), and the oxygen load of the venous blood versus the desired oxygenation of the arterial blood (the bigger the difference, the more oxygen needs to cross an oxygenator membrane). This results in a non-linear influence of the blood flow rate Q and the difference in saturation (arterial oxygen saturation level SaO2-venous oxygen saturation level SvO2). The influence depends on the oxygenator type and can be described by an oxygenator term $\text{offset}_{OXYGENATOR}$:

$$\text{offset}_{OXYGENATOR}=A\times Q+B\times(SaO2-SvO2)+C\times(Q\times(SaO2-SvO2)) \quad (21)$$

As the oxygenator term $\text{offset}_{OXYGENATOR}$ comprises a term defining the blood oxygen uptake (SaO2-SvO2), the oxygenator term constitutes a blood oxygen uptake value indicative of an amount of oxygen taken up by the blood in the oxygenator.

The coefficients A, B and C in equation 21 are determined by best fitting of test values with experimental data obtained for a given oxygenator type. To provide an illustrative example, the coefficients for equation 18 for commercially available Medtronic Fusion and Terumo RX25 oxygenators, may be in the region of $$A=-4.1192379 \quad (22)$$

$$B=1.4807944 \quad (23)$$

$$C=-1.5330679 \quad (24)$$

The coefficients depend on the oxygenator type and on the surface area and/or efficiency of the oxygenator membrane. In practice, the coefficients are obtained for a given oxygenator model by establishing the difference between $pO2_{BLOOD}$ as calculated and $pO2_{BLOOD}$ as measured by a reference method, e.g., using a conventional blood gas analyser. The difference is established in for a plurality of blood samples each oxygenated under different conditions. The oxygenation conditions may differ by the blood flow rate, temperature, pressure, haemoglobin concentration, inlet gas flow rate, inlet gas oxygen concentration, and/or venous blood oxygenation saturation. The number of blood samples is chosen to cover a wide range of values for each condition, including values that would be expected during typical use of an oxygenator and values that would not be expected in a clinical setting. Using an appropriate method, the coefficients A, B, and C are then adjusted so that the difference between the reference values (blood gas analyser values) and the calculated value for $pO2_{BLOOD}$ is minimised. For instance, the exemplary coefficients A, B, C of equations 22 to 24 have been determined on the basis of values measured from 40 samples from which a descriptive model was prepared using a least squares fitting method (using a Levenberg-Marquardt algorithm). Equation 21 is provided for illustrative purposes, and other fitting methods (e.g., mathematical models, for instance regression analysis) may be used. For instance, while the present example uses three coefficients A, B and C, a different number of coefficients may be appropriate depending on which mathematical model is used to describe the oxygenator term $\text{offset}_{OXYGENATOR}$. The coefficients can be determined off-line, during manufacture or setup. This allows the mathematical model to be optimised for a specific oxygenator, if required. The coefficients may be adjusted in the form of a retro-fit to existing equipment, e.g., as a software update. It is contemplated that the coefficients can be entered on a setup page. The setup page may be accessible to authorised personnel only.

A more accurate estimate $pO2_{EST}$ of the partial oxygen pressure is obtained by applying the temperature term $\text{offset}_{TEMP}$ and/or the oxygenator term $\text{offset}_{OXYGENATOR}$ to the partial pressure $pO2_{GE}$ as determined via equation 1.

$$pO2_{EST}=pO2_{GE}+\text{offset}_{TEMP}+\text{offset}_{OXYGENATOR} \quad (25)$$

Thus, a more accurate estimate $pO2_{EST}$ can be understood as an output of the partial pressure of oxygen in the arterial blood, which output is generated by way of equation 25 on the basis of an estimate of the partial pressure of oxygen in the exhaust gas (the estimate being constituted by $pO2_{GE}$) and on the basis of a blood oxygen uptake value (the blood oxygen uptake value being constituted by the term $\text{offset}_{OXYGENATOR}$ which is indicative of the amount of oxygen taken up in the oxygenator).

In use, various parameters of the clinical setting may cause an operational offset between the estimate $pO2_{EST}$ and the actual partial pressure $pO2_{BLOOD}$ of arterial blood leaving the oxygenator. The operational offset may be taken into account by a calibration or synchronisation step in order to further improve the accuracy of the estimate.

The synchronisation involves measuring the partial pressure $pO2_{BGA}$ using a blood gas analyser and comparing the value to the estimate $pO2_{EST}$ to calculate a synchronisation offset $\text{offset}_{SYNC}$.

$$\text{offset}_{SYNC}=pO2_{BGA}-PO2_{EST} \quad (26)$$

During ventilation procedures, blood samples are routinely obtained from a patient and their blood parameters are measured, usually with a blood gas analyser that measures several blood analytes including pO2 or pCO2. It is not untypical during a ventilation procedure for two, three, or more blood samples to be taken from the patient and analysed externally (e.g., in a blood gas analyser).

The time when a blood sample is taken for routine analysis may be registered as a sampling event, to register the sample with the estimated partial pressure $pO2_{EST}$ as estimated during the sampling event. Once the values from the blood analysis are available (which may take a few minutes), these can be related to the estimated values. For instance, a processor may be configured to correlate the blood analysis values $pO2_{BGA}$ with the value for $pO2_{EST}$ as determined at the time of the sampling event, to obtain a synchronisation offset via equation 26. The synchronisation offset can be applied to all future values to provide a more accurate reading. It would also be possible to apply the synchronisation offset retrospectively, i.e., to values of $pO2_{EST}$ determined and recorded at previous points in time.

To elaborate on equation 26, the synchronisation offset $\text{offset}_{SYNC}^{SAMPLE}$ is determined from a sample value $pO2_{BGA}^{SAMPLE}$ for a partial pressure estimate calculated during the sampling event $pO2_{EST}^{SAMPLE}$:

$$\text{offset}_{SYNC}^{SAMPLE} = pO2_{BGA}^{SAMPLE} - pO2_{EST}^{SAMPLE} \quad (27)$$

Subsequent blood partial oxygen pressure values $pO2_{BLOOD}^{CURRENT}$ are then calculated by applying the offset determined via equation 27 to the subsequent pO2 estimates $pO2_{EST}^{CURRENT}$.

$$pO2_{EST}^{CURRENT} = pO2_{EST}^{CURRENT} + \text{offset}_{SYNC}^{SAMPLE} \quad (28)$$

Even though, in order to obtain the synchronisation value, a routine blood gas analysis or equivalent analysis may have to be performed, the blood partial oxygen pressure estimate obtained via equation 28 can be carried out more often than a blood sample analysis, i.e. results can be provided continuously or in defined intervals, e.g., every second.

Whenever a new blood sample is taken for a blood gas analysis, the synchronisation may be repeated. I.e., that sampling event may be registered in order to update via equation 27 the synchronisation offset value $\text{offset}_{SYNC}^{SAMPLE}$ that is then applied subsequently via equation 28.

Herein, equations (26) to (28) are explained using the example of the partial pressure pO2 of oxygen in blood, but they are equally suitable to calibrate, or synchronise, the partial pressure pCO2 of carbon dioxide in the blood. I.e., a current estimate $pCO2_{EST}^{CURRENT}$ may be obtained by a direct measurement of the fraction feCO2 of carbon dioxide in the exhaust gas, and by relating this to the atmospheric pressure as set out in equation (3).

In this regard, the effect of any ambient air drawn into the exhaust gas on the fraction feCO2 of carbon dioxide in the exhaust gas can be neglected. For practical purposes, it can be assumed that the carbon dioxide fraction in air is close to 0%, as carbon dioxide in air typically varies between 450 ppm and 600 ppm (ppm=parts per million), whereas the fraction feCO2 of carbon dioxide in the exhaust gas is between 1% and 10%. Given the differences in magnitude, an inaccuracy resulting from ignoring carbon dioxide in air may amount to 0.045 to 0.06%, which is negligible. The amount of ambient air drawn into the exhaust gas may vary considerably if the exhaust gas flow rate is not adjusted relative to the oxygenation gas flow rate.

The values of pCO2 and pO2 thus obtained are related to the oxygen consumption and carbon dioxide production and, therefore, provide an empirical, or measurement-based, basis for optimising the composition of the oxygenation gas and for optimising the flow rate into the oxygenator. In particular, this allows the composition and/or the flow rate to be adjusted according to the development of a patient. This facilitates an unsupervised, or automated, oxygenation of a patient, which is believed to be particularly useful for long-term ventilation of a patient.

Determining pO2 by Direct Measurement

As an alternative to determining $pO2_{BLOOD}$ via equation 5 using the algorithms set out above, the applicant discovered that the blood partial oxygen pressure $pO2_{BLOOD}$ may be related to the exhaust gas partial oxygen pressure $pO2_{GE}$ directly.

Measuring $pO2_{GE}$ directly requires no knowledge of the inlet gas properties (GI, fiO2, fiCO2) or of other (non-O2) exhaust gas properties (such as feCO2). However, if measured directly, $pO2_{GE}$ is affected by the amount of gas passing through any ventilation ports or auxiliary ports of the oxygenator and, thus, cannot be assumed to directly relate to the unconsumed oxygen in the inlet gas at the point it exits the gas-blood interface inside the oxygenator. As an aside, commercial pO2 sensors may provide the value of $pO2_{GE}$ as a percentage, based on the assumption that the reading is taken with reference to unity atmospheric pressure (1 atm=1013 mbar).

Using a sensor system capable of measuring blood temperature $T_{BLOOD}$, blood flow Q, and arterial and venous blood saturation SaO2 and SvO2, adjustment terms equivalent to equations 20 and 21 above can be calculated, to provide an estimated partial pressure $pO2_{EST}$ for the blood partial oxygen pressure.

$$\text{offset}_{TEMP} = 2 \times (37 - T_{BLOOD}) \quad (29)$$

$$\text{offset}_{OXYGENATOR} = A \times Q + B \times (SaO2 - SvO2) + C \times (Q \times (SaO2 - SvO2)) \quad (30)$$

$$pO2_{EST} = pO2_{GE} + \text{offset}_{TEMP} + \text{offset}_{OXYGENATOR} \quad (31)$$

Coefficients A, B, and C are determinable as set forth above. In particular, as the oxygenator term $\text{offset}_{OXYGENATOR}$ comprises a term defining the blood oxygen uptake (SaO2–SvO2), the oxygenator term constitutes a blood oxygen uptake value indicative of an amount of oxygen taken up by the blood in the oxygenator. Likewise, $pO2_{EST}$ can be understood as an output of the partial pressure of oxygen in the arterial blood, which output is generated by way of equation 31 on the basis of an estimate of the partial pressure of oxygen in the exhaust gas (the estimate being constituted by $pO2_{GE}$) and on the basis of a blood oxygen uptake value (the blood oxygen uptake value being constituted by the term $\text{offset}_{OXYGENATOR}$ which is indicative of the amount of oxygen taken up in the oxygenator).

Embodiments of the present invention may include a sensor system that is configured to continuously determine an estimate of the partial pressure $pO2_{GE}$ of oxygen in the exhaust gas, either by way of a measuring the input values required for equations 1-19 and a processor configured to process equations 1-19, or by direct measurement of the partial oxygen pressure $pO2_{GE}$ in the exhaust gas. In practice, the system may record values in defined intervals, e.g. every second.

The system may be configured to apply a temperature term $\text{offset}_{TEMP}$ and/or the oxygenator term $\text{offset}_{OXYGENATOR}$ to calculate an estimated partial pressure $pO2_{EST}$ in accordance with equation 25 or 31.

For synchronisation, the sensor system may be configured to register a sampling event. A sampling event occurs when a blood sample is taken, and pO2 and/or pCO2 estimates determined at the time of the blood sampling can be associated with the blood sample. In a clinical setting, it may take a few minutes until blood sample values are available. During this time, the sensor system is able to continue determining pO2 and/or pCO2 estimates. Once the values from the blood analysis are available, these can be entered into the sensor system. The sensor system is configured to correlate the blood analysis values with the pO2 and/or pCO2 estimates determined during the sampling event. This allows any deviation between the blood value and the estimate to be determined, and a synchronisation value can be applied to the sensor values. It is then possible to apply the synchronisation value to future pO2 and/or pCO2 estimates determined by the sensor system.

In this manner, a large number of readings can be taken, whereas it would not be practical to take and analyse a large number of blood samples. The pO2/pCO2 estimates can be determined continuously or in defined intervals.

Multiple sampling events may be registered, whenever appropriate, e.g. according to the number of blood samples taken during an intervention, in order to update the synchronisation offset.

By applying a synchronisation offset, a more accurate determination of the arterial partial oxygen pressure $pO2_{BLOOD}$ to be made based on the estimate derived from the partial oxygen pressure $pO2_{GE}$, which can be obtained without blood contact. Likewise, the partial pressure of carbon dioxide may be determined. As such, the described sensor system may be part of, or constitute, a monitoring system of the present invention.

Temperature Considerations

Because the reading of many blood analytes is dependent on temperature, the blood gas values of pO2 and pCO2 are typically obtained at a standardised temperature. Most blood gas analysers set the blood sample temperature to 37° C. as the standardised temperature.

However, also the partial pressures pO2 and pCO2 are temperature-dependent. It is often the case that the blood circulating in the oxygenator has a different temperature than the temperature-controlled sample in the blood gas analyser. For instance, the body temperature and blood of a patient may be cooled to significantly below 37° C. during surgery, whereas a blood gas analyser may routinely warm the blood to 37° C. In contrast, any values obtained by sensors from the oxygenator will be close to the patient temperature. Any difference between the blood temperatures needs to be taken into account.

A suitable temperature adjustment to obtain a temperature-adjusted value $pO2_{ADJ}$ or $pCO2_{ADJ}$, respectively, may be obtained using known equations.

$$pO2_{ADJ} = pO2_{BLOOD}10^{\left(\frac{0.0252}{0.234\left(\frac{pO2_{BLOOD}}{100}\right)^{3.88}+1}+0.00564\right)*(t-37)} \quad (32)$$

$$pCO2_{ADJ} = pCO2_{BLOOD}10^{(0.019)*(t-37)} \quad (33)$$

Equation 32 corresponds to the formula used by the Radiometer AML-3, and equation 33 corresponds to the formula used by Corning Models 178, 170, 168 and 158, both reported by Edward R. Ashwood in Clinical Chemistry Vol 29 No 11, pg 1877 (1993).

Figure 1:
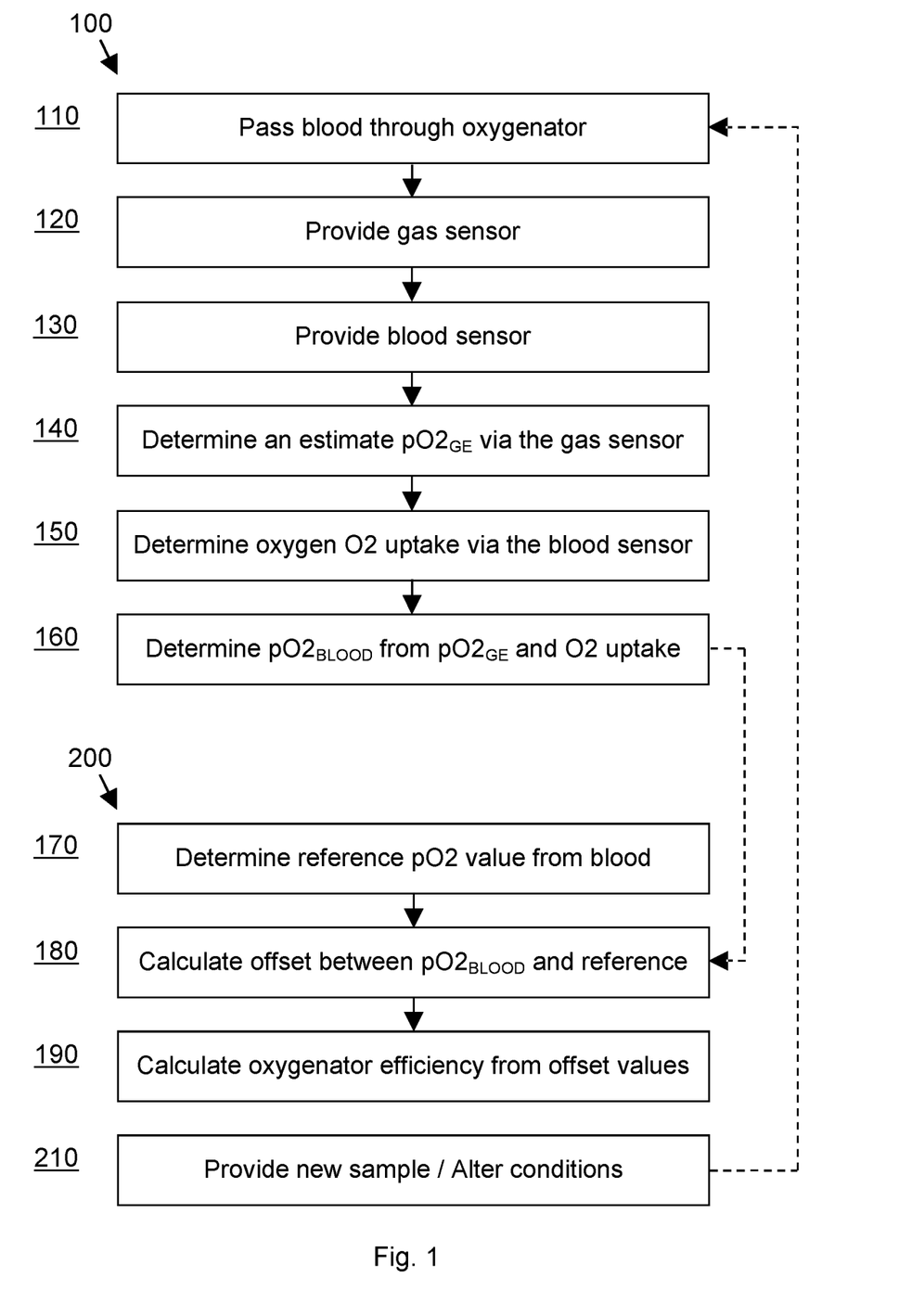
FIG. 1 shows steps of an exemplary sequence of steps of a method for determining the partial pressure of oxygen in arterial blood, described herein for the understanding of embodiments of the invention.

Exemplary Procedure of Determining the Partial Pressure of Oxygen in Arterial Blood Turning to FIG. 1, a sequence of steps of a method 100 in accordance with the above principles are shown. In step 110, blood is provided for oxygenation through an oxygenator. In step 120, a sensor system is provided suitable for determining one or more gas values. In step 130, a sensor system is provided suitable for determining one or more blood values. In step 140, one or more gas values are determined, the gas values comprising an estimate of the partial pressure of oxygen in the exhaust gas of the oxygenator. In step 150, one or more blood values are determined, the blood values comprising a blood oxygen uptake value indicative of an amount of oxygen taken up by the blood in the oxygenator. In step 160, an output is generated by using the blood oxygen uptake value to adjust the estimate of the partial pressure of oxygen in the exhaust gas.

Some or all steps of method 100 may be carried out to implement one or more of the algorithms described above.

Step 150 may comprise measuring the venous oxygen saturation of the blood entering the oxygenator, measuring the arterial oxygen saturation of the blood leaving the oxygenator, and calculating the blood oxygen uptake value as a function of the difference between the arterial oxygen saturation and the venous oxygen saturation.

Step 150 may comprise measuring the flow rate, the temperature, and/or the haemoglobin concentration of the blood passing through the oxygenator. Step 150 may comprise calculating the blood oxygen uptake value as a function of the flow rate, the temperature, and/or the haemoglobin concentration. Step 160 may comprise calculating the output as a function of the flow rate, the temperature, and/or the haemoglobin concentration.

Step 140 may comprise obtaining a measurement of the partial pressure of oxygen in the exhaust gas and using the measurement as the estimate.

Step 140 may comprise determining the amount of oxygen in the exhaust gas and the amount of exhaust gas leaving the oxygenator, determining the fraction of oxygen in the exhaust gas as a quotient of the amount of oxygen in the exhaust gas and the amount of exhaust gas, and deriving the estimate of the partial pressure of oxygen in the exhaust gas from the fraction of oxygen in the exhaust gas.

Step 140 may further comprise determining an inlet gas value indicative of the amount of oxygen entering the oxygenator. Step 160 may comprise determining the amount of oxygen in the exhaust gas based on the difference between the inlet gas value and the blood oxygen uptake value.

Step 140 may comprise measuring one or more of the total amount of the oxygenation gas, the amount or fraction of oxygen in the oxygenation gas, the amount or fraction of carbon dioxide in the oxygenation gas, and the amount or fraction of carbon dioxide in the exhaust gas.

Included in FIG. 1 is a method 200 for characterising the oxygenation efficiency of an oxygenator. The method 200 employs the steps of method 100 for a plurality of blood samples.

In step 170, a reference value of the partial pressure of oxygen in the arterial blood is obtained using a reference method, such as by measuring the blood in a conventional blood gas analyser.

In step 180, an offset value is calculated to describe the difference between the output generated in step 160 and the reference value measured in step 170. The offset value may be used to adjust the output.

In step 190, one or more coefficients for a model describing the oxygenation efficiency of an oxygenator are calculated based on multiple offset values.

In step 210, a blood sample or blood volume is provided for oxygenation in the oxygenator, and one or more of the conditions for steps 110 to 160 are altered, before steps 110 to 160 are repeated.

Flow-Control Oxygenator

The algorithms above apply to oxygenators that are conventional in the sense that the amount/proportion of gas or ambient air passing through auxiliary/ventilation ports is treated as an unknown quantity, and so the amount of exhaust gas GE and any components therein are not directly relatable to the amount of exhaust gas exiting the gas-blood interface inside the oxygenator.

For the understanding of some embodiments, described herein is an unconventional oxygenation system that allows the flow rates of oxygenation gases into an oxygenator and/or of exhaust gases out of an oxygenator to be determined by control of gas flow parameters. Herein, such an unconventional oxygenation system may be referred to as a "flow-control" oxygenation system. The flow-control oxygenation system disclosed herein is described in the applicant's co-pending United Kingdom patent application number GB1421498.5.

Embodiments of the present invention may be incorporated in, or make use of, a flow-control oxygenation system. This provides a means allowing the flow rate ("sweep") and/or the fraction of oxygen of the supply gas into the oxygenator to be controlled. Also, the flow rate of the exhaust gas GE out of the main oxygenator exhaust port may be considered in the determination of blood or oxygenation gas parameters. For instance, instead of determining GE by way of equation 19 above, it may be possible to derive an estimate of GE from flow control parameters.

In one operating mode, a flow-control oxygenation system may allow a flow rate to be applied that sucks only a fraction of the gas leaving the gas-blood interface. Any remaining amount of exhaust gas would leave the oxygenator via the ventilation ports. In that case, the composition of the fraction of the exhaust gas through the oxygenator exhaust port will closely correspond to the composition of the gas leaving the gas-blood interface inside the oxygenator, because it is not diluted by ambient air drawn in via the ventilation ports. This will allow a more accurate measurement to be made of the fraction of a component of the exhaust gas, such as the fraction feO2 of oxygen in the exhaust gas or the fraction feCO2 of carbon dioxide in the exhaust gas. This operating mode may be appropriate if there is no concern about unused oxygenation gas leaking out of the oxygenator, for instance during extracorporeal ventilation without anaesthesia.

In one operating mode, a flow-control oxygenation system may allow a flow rate high enough to suck all of the exhaust gas leaving the gas-blood interface inside the oxygenator, and also ambient air drawn into the oxygenator housing via ventilation ports. In that case, the composition of the exhaust gas through the oxygenator exhaust port includes ambient air. This operating mode may be appropriate if passage of unused oxygenation gas (e.g., comprising unused anaesthetic agent) out of the oxygenator is of concern. This operating mode may also be necessary to achieve sufficiently accurate measurements if the flow rate of oxygenation gas into the oxygenator is low. With knowledge of the composition of the ambient air and knowledge of the flow rate of the oxygenation gas entering the oxygenator, the oxygen concentration just after the gas-blood interface may be determined.

Values determined via the different operating modes, e.g. the fraction of an exhaust gas component or the amount of exhaust gas, may be used to solve the algorithms above.

In particular, the applicant contemplates that the various methods described herein may be used in a complementary fashion. For instance, in a flow-control oxygenator, the flow rate of the exhaust gas GE may be determined both via equation 19 above and via derivation from flow-control parameters.

Components Overview of a Flow-Control Oxygenation System

Figure 2:
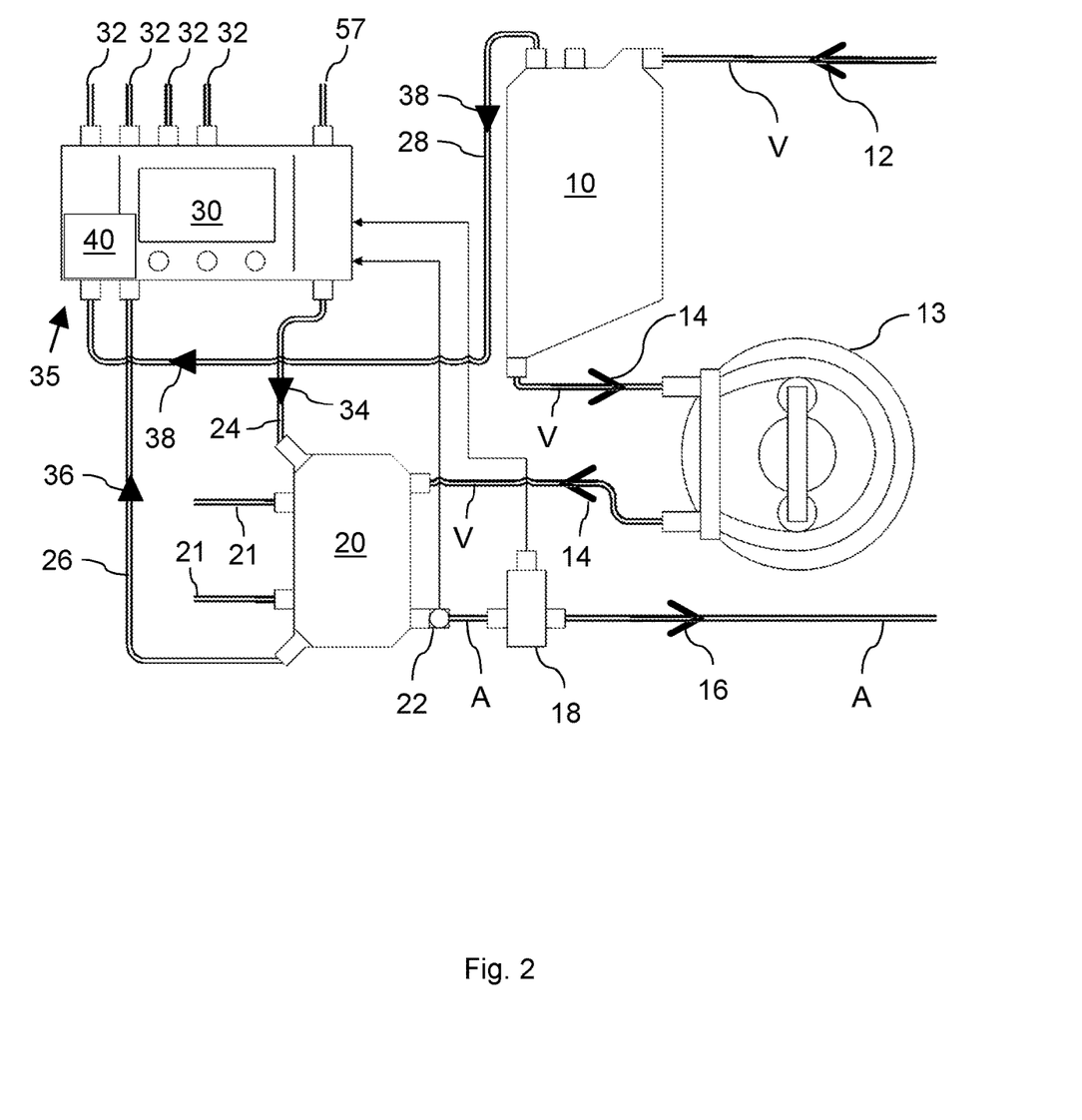
FIG. 2 shows a schematic layout of components of an exemplary ventilation system described herein for the understanding of embodiments of the invention.

FIG. 2 provides an overview of system components of a flow-control ventilation system for use with embodiments of the present invention. A pulmonary (blood) bypass loop crosses a gas (oxygen) line. The pulmonary bypass loop circulates blood from a patient in order for the blood to be oxygenated and to be returned to the patient. The gas line provides the oxygenation gas for blood oxygenation.

Pulmonary Bypass Loop (Blood)

Venous blood from a patient (not shown in FIG. 2) is circulated in the direction indicated by arrow 12 towards a reservoir 10 via a venous line V. From the reservoir 10, the venous blood is pumped by a pump 13 in the direction indicated by arrows 14 towards an oxygenator 20. In the oxygenator 20, the blood is oxygenated. Blood leaves the oxygenator 20 to be supplied, as arterial blood, via an arterial line A in the direction indicated by arrow 16 towards a patient. A flow sensor 18 is provided to measure the flow rate of the re-oxygenated blood exiting the oxygenator 20. A temperature sensor 22 is provided to measure the temperature of the re-oxygenated blood exiting the oxygenator 20. Water lines 21 connect the oxygenator 20 to a water bath for maintaining a predefined temperature.

Oxygenation Gas Line

A gas circulator 35 comprises a blender 30 for preparation of oxygenation gases. In the particular depiction, the blender also comprises a vacuum subsystem 40 for removal of exhaust gases. However, conventional oxygenation gas blending systems do not comprise a vacuum sub-system.

Gases, such as nitrogen (N2) and oxygen (O2) of predetermined purity levels are supplied from hospital supply lines 32 into a blender 30. Compressed air with a composition of about 79% nitrogen and 21% oxygen may be supplied. Hospital-supplied gases may contain traces of carbon-dioxide and/or noble gases. The hospital mains also provide a source of low pressure or vacuum. The hospital supplies may also include oxygenation gas of a predetermined composition or oxygen at a predetermined purity level, which may be supplied via a supply line 57 to the blender 30.

In the blender 30, the gases are mixed to a composition that is to be supplied to the oxygenator 20 and fed in the direction indicated by arrow 34 via a supply line 24. In the oxygenator 20, the haemoglobin molecules of the venous blood are to take up oxygen and to release carbon dioxide. In the oxygenator 20, other gases, such as waste anaesthetic gases, may be released from or not be taken up in the oxygenator. Any gases released in or passing through the oxygenator 20 and gas components not taken up from the inlet gas are collected as waste gas or exhaust gas and leave the oxygenator 20 via an exhaust line 26 in the direction of arrow 36 and are transported away. The gas flow via the exhaust line 26 is assisted by a vacuum. In the embodiment described herein, the vacuum is supplied via a vacuum subsystem 40 that is part of the gas circulator 35. Conventionally, an oxygenator is connected directly to a hospital vacuum port.

Components Operation

The operation of the oxygenator 20, the blender 30 and the vacuum sub-system 40 will now be described in more detail with reference to FIGS. 3, 4, 5 and 6.

Oxygenator 20

Figure 3:
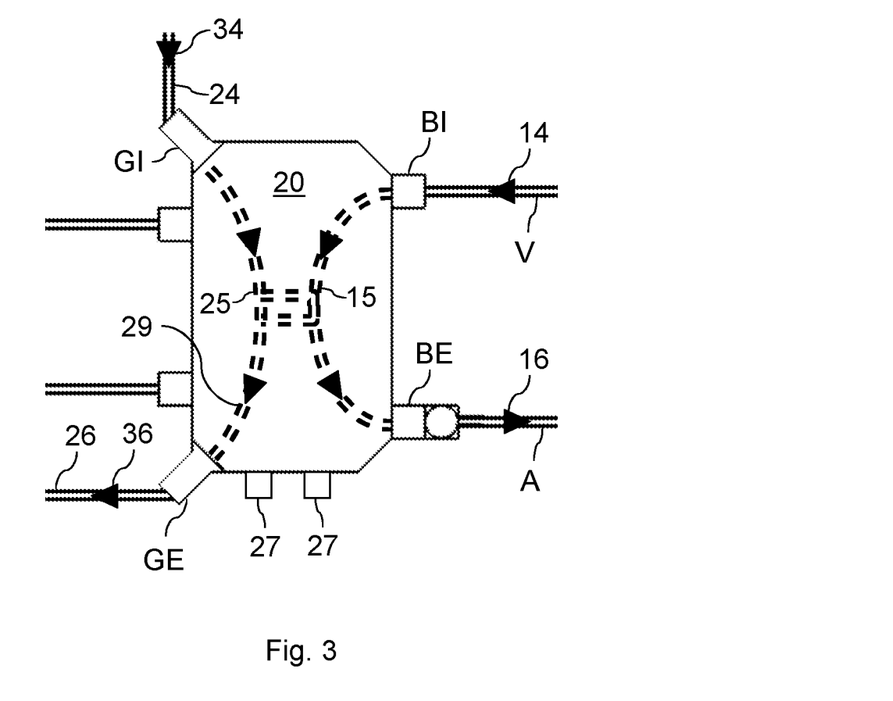
FIG. 3 shows an oxygenator of an exemplary ventilation system described herein for the understanding of an embodiment of the invention.
Figure 4:
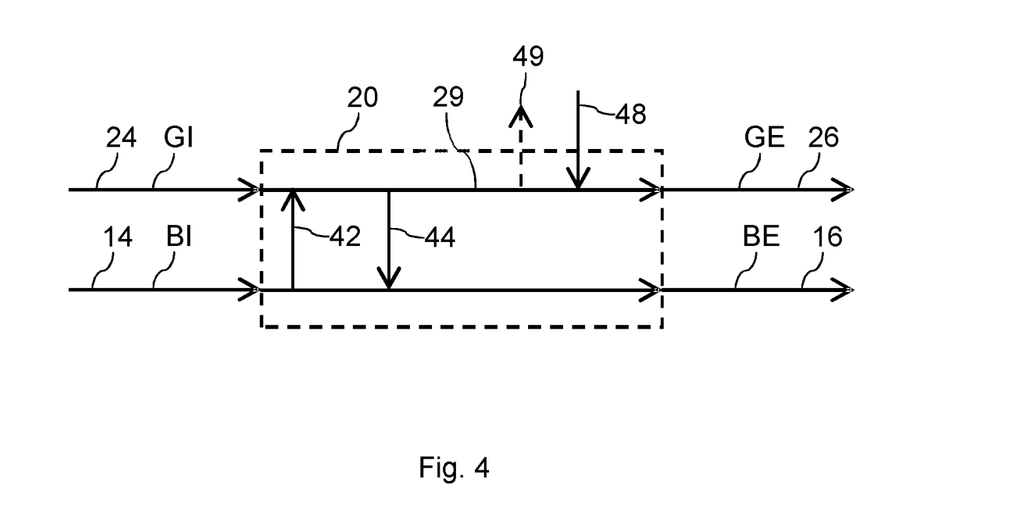
FIG. 4 shows a schematic flow analysis for the FIG. 3 oxygenator, described herein for the understanding of embodiments of the invention.

Venous blood carrying CO2 enters the oxygenator 20 via venous line V (in direction 14), as shown in detail in FIGS. 3 and 4. Venous blood enters the oxygenator 20 in a condition indicated herein by the symbol BI. In particular, the blood transports an amount of oxygen BIO2 and an amount of carbon dioxide BICO2 per unit of time.

FIG. 3 illustrates the uptake of oxygen by the blood in the oxygenator 20. The venous blood is transported within the oxygenator 20 along line 15 and exposed to the gas mixture, inlet gas GI from the blender 30, that is transported along the line 25. The gas mixture GI has a higher oxygen partial pressure and a lower carbon dioxide partial pressure than the blood, causing the haemoglobin to release CO2 and take up O2. Note that although FIG. 3 indicates, schematically, a concurrent exchange, oxygenators use, in practice, a countercurrent exchange.

FIG. 4 illustrates a flow diagram. In the oxygenator 20, CO2 is released from the blood into the gas stream, as indicated by arrow 42. The blood stream takes up O2 in a reaction indicated by arrow 44. Other components, such as waste anaesthetic gas, may not be taken up by the blood and enter or remain in the exhaust gas stream as indicated by arrow 46. Oxygenated blood is referred to as arterial blood.

The oxygenator 20 is not an air-tight unit. It may comprise one or more secondary (i.e., ventilation) exhaust ports 27 as a failsafe measure, to avoid pressure build-up within the oxygenator 20 if the exhaust line 26 is blocked. As the secondary exhaust ports 27 permit passage of air or gases, the amount of exhaust gas GE leaving the oxygenator 20 at the exhaust line 26 cannot be assumed to be identical to the amount of exhaust gas at a point 29 immediately downstream of the gas-blood interface inside the oxygenator 20.

As or if a vacuum-induced flow is applied via exhaust line 26, this draws, therefore, not only exhaust gas GE from the oxygenator 20, but also ambient air 48 via secondary exhaust ports 27. To provide an illustrative example, for every 2 L of gas mixture supplied into the oxygenator 20 via supply line 24, 2.1 L of exhaust gas may be drawn through exhaust line 26.

The difference in flow rates that causes ambient air 48 to be drawn into the oxygenator 20 can also be used to ensure that any waste anaesthetic gas 46 is removed via the exhaust line 26. Thus, waste anaesthetic gas 46 is prevented from seeping out of the oxygenator 20, as indicated by arrow 49, into the operating theatre, where anaesthetic gases could affect staff.

Arterial blood leaves the oxygenator 20 in a condition BE. The amount of oxygen of the arterial blood BEO2 is related to the arterial oxygen saturation SaO2 and also depends on the haemoglobin concentration in the blood.

Exhaust gas GE which carries components released from the blood, such as CO2 from transfer 42, or waste anaesthetic gas that has not been taken up inside the oxygenator 20, is drawn via exhaust line 26 towards the vacuum sub-system 40 of gas circulator 35.

Blender 30

Figure 5:
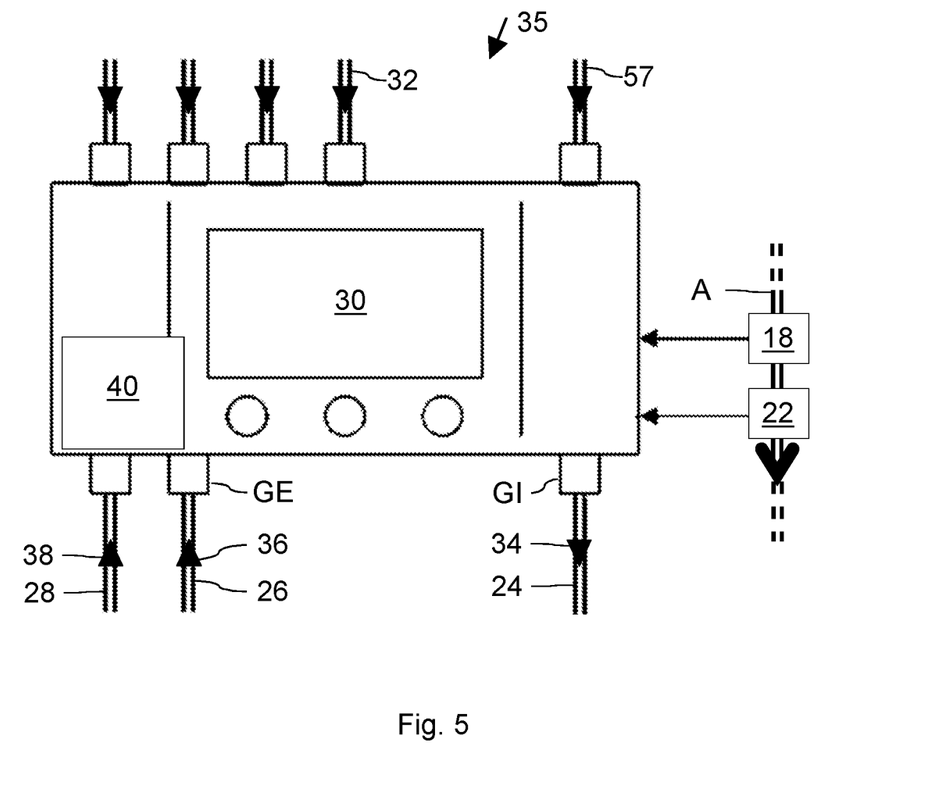
FIG. 5 shows a gas blender for use with a ventilation system, described herein for the understanding of embodiments of the invention.

In FIG. 5, the blender 30 is drawn enlarged as part of the gas circulator 35. Gas components supplied via inlets 32 are mixed to provide a supply gas for the oxygenator 20. The processing steps in the blender 30 are set out in FIG. 6. Hospital-supplied gases 32 are fed first into a gas mixer 52, and then passed through a flow control 54, a failsafe control 56, and sensors 58, before being supplied via supply line 24 to the oxygenator 20.

Gas Mixer 52

Figure 6:
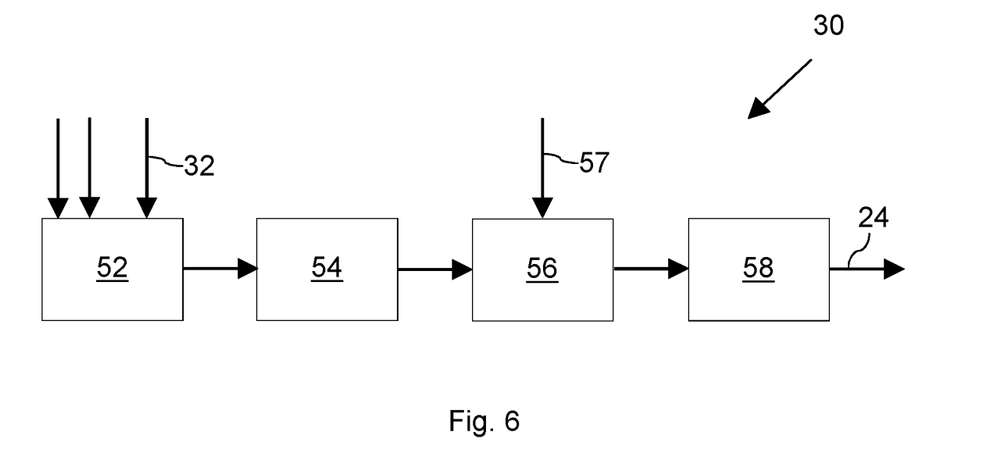
FIG. 6 shows a schematic flow chart of the blender gas supply, described herein for the understanding of embodiments of the invention.

The gas mixer 52 comprises a mixing chamber into which component gases are received via an inlet and mixed to an oxygenation gas. The mixing chamber constitutes a blending unit in which the component gases are blended into an oxygenation gas. The mixing chamber also constitutes a holding unit or reservoir in which component gases may homogenise. The gas pressure may be controlled via a back pressure regulator. Excess gas may be vented into the atmosphere. From the mixing chamber of the gas mixer 52, the oxygenation gas passes through the blender flow control 54.

Blender Flow Control 54

The blender flow control 54 allows the flow rate of the gas mixture, the oxygenation gas, to be adjusted to a pre-determined flow rate. The blender flow control 54 controls the flow rate of the oxygenation gas from the holding unit, or mixing chamber, and thus constitutes a flow controller suitable for controlling the supply gas parameters in accordance with embodiments of the invention. This allows the amount of gas supplied to the oxygenator to be set, and allows this to be used in the calculation of oxygenation-related parameters.

A flow control unit in the blender allows the flow rate of the gas mixture to be set to low rates after it has been mixed as required. This improves the accuracy of the composition particularly at low flow rates, which are preferred in pulmonary systems.

It is difficult to achieve a good quality mixture of the oxygenation gas when throttling the flow rate of the hospital-supplied gas. Thus, to obtain an accurate mixture, the hospital-supplied gas is fed at a suitably high flow rate. The flow control therefore addresses the problem of how to obtain an accurately mixed oxygenation gas, while also providing the oxygenation gas to the oxygenator 20 at a low flow rate.

To illustrate this with an example, both oxygen and nitrogen may be supplied at 1.05 L/min. A 50%/50% mixture of these two gases would create a volume flow of 2.1 L/min (1.05 L/min+1.05 L/min=2.1 L/min). If, for instance, it is desired to supply only 2.0 L/min oxygenation gas to the oxygenator, the excess of 0.1 L/min (2.1 L/min-0.1 L/min=2.0 L/min) is vented, or "bled", into the atmosphere. Any suitable mixing ratios may be used in practice.

Failsafe Control 56

The failsafe control 56 provides an additional safety feature, by providing an option to switch to an external gas supply 57. In particular, the failsafe control 56 may be responsive to the gas mixer 52, the blender flow control 54, and/or sensors 58, and is configured to switch to the external gas supply 57 oxygen in the event one of the gas mixer 52 or the blender flow control 54 fail to provide oxygenation gas of pre-determined composition or flow rate.

The gas supplied via the external gas supply 57 may be pure oxygen. The gas supplied may be provided by a mechanical blender, or an emergency backup gas supply.

Sensors 58/Output Measurement

The sensors 58 are configured to measure parameters of the supply gas mixture. The parameters include the flow rate of the gas mixture, the pressure of the gas mixture, the temperature of the gas mixture, the oxygen concentration, the carbon dioxide concentration, or combinations thereof.

The values obtained by the output measurement can be checked against expected values and countermeasures can be taken in the event of any discrepancy. For instance, the flow rate as determined by sensors 58 can be compared to the flow rate set by the blender flow control 54. In the event of any discrepancy, countermeasures can be taken. Countermeasures include the generation of a notification signal, the increase or decrease of the flow rate by the blender flow control 54, or the switching to an external gas supply 57 by the failsafe control 56.

The sensors 58 allow the composition, pressure, temperature, and flow rate to be monitored regardless of the source, e.g., whether this is from gas mixer 52 or from an external gas supply 57.

The oxygenation gas of known properties leaves the blender 30 via an outlet to be supplied to the oxygenator 20.

This allows a controller to control parameters of the oxygenation gas supply to the oxygenator. For instance, the flow controller allows the total flow rate, or "sweep", of the gas supplied into the oxygenator to be controlled. Likewise, this allows the fraction of oxygen supplied into the oxygenator to be controlled.

Vacuum Subsystem 40

Vacuum may be used to create a flow gradient to assist gas flow. In the system described herein, the vacuum pressure gradients are controlled by a vacuum subsystem 40 which in turn is supplied from a single vacuum supply, e.g. from a hospital.

The flow gradient in the exhaust line 26 is indicated by arrow 36 and pulls exhaust gas from the oxygenator 20.

To illustrate this with an example, supply gas GI may be supplied to the oxygenator 20 at a rate of 2 L/min. The vacuum sub-system may be set to withdraw exhaust gas at a flow rate of 2.1 L/min. Thus, it can be assumed that, absent any influences by the blood oxygenation processes, 0.1 L/min (0.1 L/min=2.1 L/min exhaust gas−2.0 L/min inlet gas) of ambient air were drawn in via the oxygenator.

The combination of the blender 30 and the vacuum sub-system 40 in a gas circulator 35 facilitates the integration of sensors and the evaluation of measured properties of the oxygenation gas and the exhaust gas (e.g., flow rate, pressure, temperature, composition, oxygen fraction, carbon dioxide fraction, and combinations thereof).

Although the gas supply 32 and 57 is described herein as being provided by a hospital, this is exemplary for a typical setting. The gas supply may be provided by another source. Any number and type of supply gases may be used, according to requirements.

Figure 7:
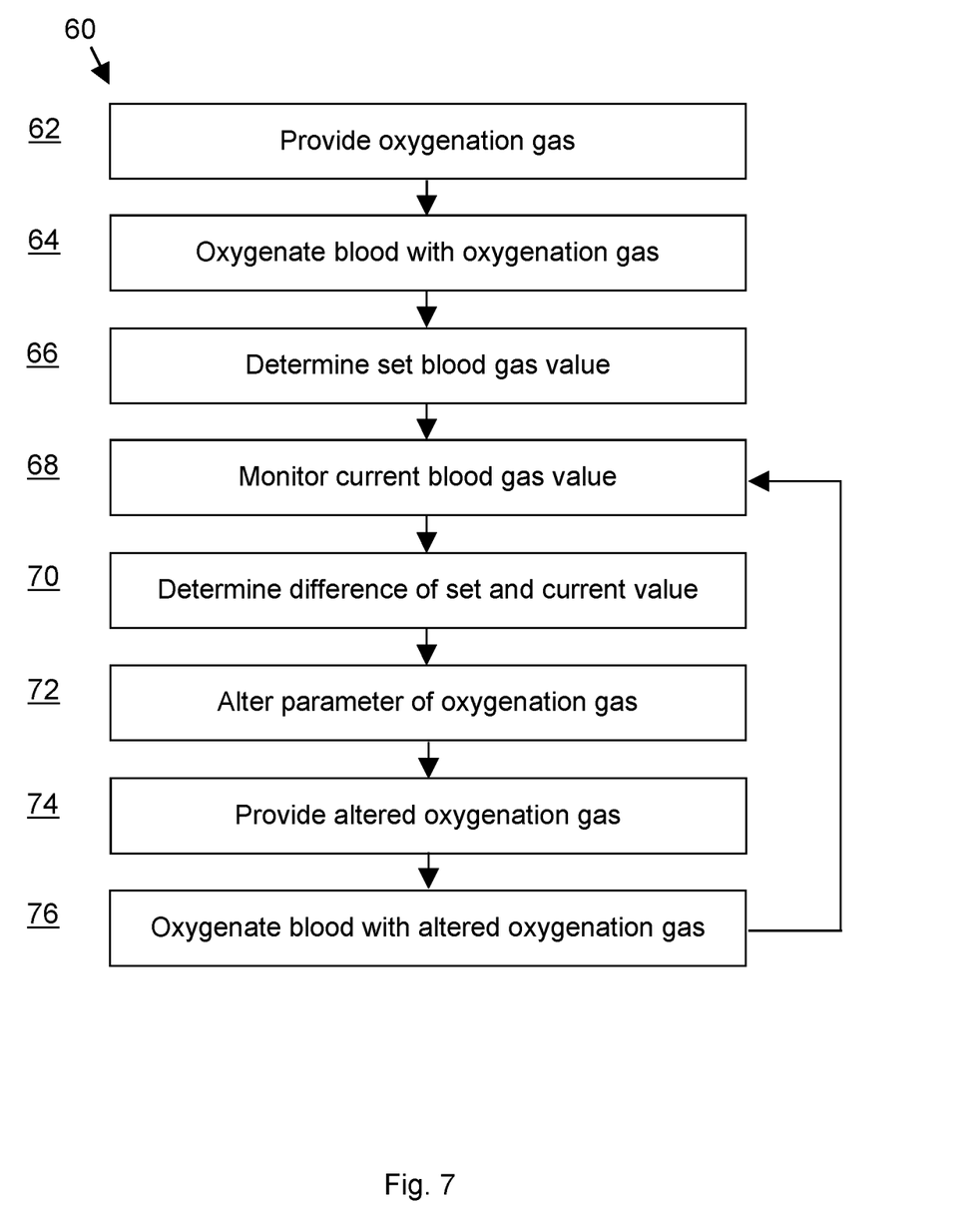
FIG. 7 shows an exemplary sequence of steps of a method for controlling blood gas level, in accordance with embodiments of the invention.

FIG. 7 illustrates steps of a method 60 for controlling a blood gas value, such as the partial pressure of oxygen, or carbon dioxide, or both, in arterial blood. In step 62, an oxygenation gas is provided at a flow rate and with a composition comprising an oxygen fraction. In step 64, the oxygenation gas is used in an oxygenator to oxygenate venous blood to generate arterial blood. In step 66, the level of one or more blood gas values of the arterial blood exiting the oxygenator is determined as the set blood gas level. This may be done using one or more of the above-described methods. In step 68, while the oxygenator continues to oxygenate blood, one or more current blood gas levels of the arterial (oxygenated) blood exiting the oxygenator are monitored. In step 70, it is determined whether or not there is a difference between the current blood gas level and the set blood gas level. If there is a difference, then, in step 72, one or more parameters of the oxygenation gas are adjusted. For instance, the flow rate and/or the oxygen fraction may be altered. In step 74, the oxygenation gas with the altered flow rate or composition is supplied to the oxygenator, and in step 76, the blood is oxygenated by oxygenation gas with the altered parameters. This will result in an adjustment of the levels of the blood gas values. The method 60 continues to monitor the blood gas levels and alters the oxygenation gas if an adjustment is required.

Illustrative Example

In practice, a clinician (perfusionist) may start a perfusion treatment with initial perfusion parameters based on clinical expertise, taking into account patient size, age, clinical requirements, etc. Perfusion may then be performed and the system may settle, i.e., blood gas values including the partial pressure pO2 of oxygen and the partial pressure pCO2 of carbon dioxide may settle at a value. The value may be acceptable to the clinician or not, if not, the clinician may manually adjust perfusion parameters to improve the response of the patient. The manual adjustment may be too weak or to strong, and may have to be repeated until a desired clinical response is observed. Note that a clinician is likely to be interested in a clinical response, rather than setting a particular blood gas level value.

If a clinician is content with the perfusion performance, e.g. because blood gas values are within clinically acceptable boundaries, the control system of the invention may be instructed to take over. Using the monitoring arrangement, the control system may determine one or more blood gas values in the arterial blood, as set by the clinician. The blood gas value may be a level of the partial pressure of oxygen in the arterial blood. The blood gas value may be a level of the partial pressure of carbon dioxide in the arterial blood. The blood gas values thus determined may be stored as a value indicating a pre-determined level.

The monitoring arrangement continues to monitor the blood gas values. The control system comprises a configuration permitting it to change the flow rate of the oxygenation gas and/or the fraction of oxygen in the oxygenation gas, in order to adjust the gas values in response to changes of the blood gas values. If a change of blood gas values is detected, the control system changes the flow rate and/or the fraction of oxygen accordingly, to adjust the blood gas values towards the pre-determined level.

The pre-determined level may be determined by analysing the arterial blood, e.g. the blood exiting the oxygenator, or by using any of the above-described methods. The pre-determined level for each blood gas value may be set via an interface.

The control mechanism improves the responsiveness of the perfusion system. This further allows the blood gas values to be maintained at a pre-determined level, or within pre-determined boundaries. This eliminates the risk of fluctuations. This improves the safety of the perfusion system. The control system of the invention may allow pro-longed periods of unsupervised perfusion.

The invention claimed is:

1. A control system controlling at least one blood gas value in blood processed by an oxygenator of an extracorporeal perfusion system, wherein the oxygenator is configured to generate arterial blood by exposing venous blood to oxygen from an oxygenation gas supply, the control system comprising:
 a monitoring arrangement to determine a level of the at least one blood gas value in the arterial blood,
 a blender having a plurality of gas inlets and a mixing chamber operable to provide the oxygenation gas supply, and
 a controller responsive to the monitoring arrangement, the controller configured to control parameters of the oxygenation gas supply to the oxygenator, to adjust at least one of the blood gas values toward a pre-determined level, and wherein the controller comprises a configuration permitting it to alter the composition and a flow rate of the oxygenation gas supplied to the oxygenator, wherein the controller is configured to simultaneously control the partial pressure of oxygen in the arterial blood and the partial pressure of carbon dioxide in the arterial blood by setting the flow rate of the oxygenation gas supply from the mixing chamber to a level suitable for adjusting the partial pressure of carbon dioxide, and at the set flow rate, setting the fraction of oxygen in the mixing chamber so that the fraction of oxygen in the oxygenation gas supply is at a level suitable for adjusting the partial pressure of oxygen.

2. The control system according to claim 1, wherein the blood gas values comprise at least one of (a) the partial pressure of oxygen in the arterial blood and (b) the partial pressure of carbon dioxide in the arterial blood.

3. The control system according to claim 1, wherein the controller is configured to adjust the partial pressure of carbon dioxide in the arterial blood by altering the flow rate of the oxygenation gas supply.

4. The control system according to claim 1, wherein the controller is configured to adjust the partial pressure of oxygen in the arterial blood by altering the fraction of oxygen in the oxygenation gas supply.

5. The control system according to claim 1, wherein the controller comprises decision logic to determine a difference between the level of the blood gas value and the pre-determined level, and to determine oxygenation gas supply parameters suitable for reducing the difference.

6. The control system according to claim 5, wherein the decision logic is configured to reduce the difference by calculating an offset value representing a change in oxygenation gas supply parameters suitable for reducing the difference.

7. The control system according to claim 5, wherein the pre-determined level is a pre-determined partial pressure of carbon dioxide in the arterial blood, and wherein the oxygenation gas supply parameters comprise a flow rate suitable for reducing the difference.

8. The control system according to claim 5, wherein the pre-determined level is a pre-determined partial pressure of oxygen in the arterial blood, and wherein the oxygenation gas supply parameters comprise a fraction of oxygen suitable for reducing the difference.

9. The control system according to claim 1, wherein the controller is configured to simultaneously control a plurality of parameters of the oxygenation gas supply to the oxygenator, to simultaneously adjust levels of a plurality of blood gas values.

10. A method of controlling at least one blood gas value in blood processed by an oxygenator of an extracorporeal perfusion system, wherein the oxygenator is configured to generate arterial blood by exposing venous blood to oxygen from an oxygenation gas supply, the method comprising the steps of:

determining a level of each of the at least one blood gas value in the arterial blood, delivering the oxygenation gas supply from a mixing chamber, and simultaneously controlling, in response to the level, partial pressure of oxygen in the arterial blood and partial pressure of carbon dioxide in the arterial blood by setting a flow rate of the oxygenation gas supply from the mixing chamber to the oxygenator to a level suitable for adjusting the partial pressure of carbon dioxide, and at the set flow rate, setting the fraction of oxygen in the mixing chamber to a level suitable for adjusting the partial pressure of oxygen.

11. The method according to claim 10, wherein determining a level of at least one blood gas value comprises monitoring at least one of (a) the partial pressure of oxygen in the arterial blood and (b) the partial pressure of carbon dioxide in the arterial blood.

12. The method according to claim 10, further comprising adjusting the partial pressure of carbon dioxide in the arterial blood by altering the flow rate of the oxygenation gas supply.

13. The method according to claim 10, further comprising adjusting the partial pressure of oxygen in the arterial blood by altering the fraction of oxygen in the oxygenation gas supply.

14. The method according to claim 10, further comprising
determining a difference between the level of the blood gas value and the pre-determined level, and
determining oxygenation gas supply parameters suitable for reducing the difference.

15. The method according to claim 14, further comprising
calculating an offset value representing a change in oxygenation gas supply parameters suitable for reducing the difference, and
determining the oxygenation gas supply parameters on the basis of the offset value.

16. The method according to claim 14, further comprising
determining the difference between the level of the partial pressure of carbon dioxide in the arterial blood and the pre-determined level of the partial pressure of carbon dioxide in the arterial blood, and
determining an oxygenation gas flow rate suitable for reducing the difference.

17. The method according to claim 14, further comprising
determining the difference between the level of the partial pressure of oxygen in the arterial blood and the pre-determined level of the partial pressure of oxygen in the arterial blood, and
determining an oxygenation gas oxygen fraction suitable for reducing the difference.

18. The method according to claim 10, comprising simultaneously controlling a plurality of parameters of the oxygenation gas supply to the oxygenator, to simultaneously effect an adjustment of levels of a plurality of blood gas values.

* * * * *